(12) United States Patent
Brooks

(10) Patent No.: US 6,398,409 B1
(45) Date of Patent: Jun. 4, 2002

(54) PATIENT SUPPORT WITH DIGITAL X-RAY CASSETTE

(75) Inventor: Jack J. Brooks, Folly Beach, SC (US)

(73) Assignee: Hill-Rom Services, Inc., Wilmington, DE (US)

( * ) Notice: Subject to any disclaimer, the term of this patent is extended or adjusted under 35 U.S.C. 154(b) by 0 days.

(21) Appl. No.: 09/516,266

(22) Filed: Feb. 29, 2000

Related U.S. Application Data

(60) Provisional application No. 60/142,483, filed on Jul. 6, 1999, and provisional application No. 60/124,611, filed on Mar. 16, 1999.

(51) Int. Cl.$^7$ ................................................ A61B 6/04
(52) U.S. Cl. ........................ 378/209; 378/189; 378/208; 5/600; 5/601
(58) Field of Search ................................ 378/189, 208, 378/209; 5/600, 601

(56) References Cited

U.S. PATENT DOCUMENTS

| 4,501,414 | A | * | 2/1985 | Mason et al. ................... 5/614 |
| 4,584,989 | A | * | 4/1986 | Stith ............................. 600/18 |
| 4,589,124 | A | * | 5/1986 | Ruiz ............................ 378/178 |
| 4,665,574 | A | * | 5/1987 | Filips et al. .................... 5/694 |
| 4,847,929 | A | * | 7/1989 | Pupovic ......................... 5/608 |
| 4,893,323 | A | * | 1/1990 | Cook, III ..................... 378/208 |
| 4,905,266 | A | * | 2/1990 | Kuck et al. ................... 378/177 |
| 5,016,268 | A | * | 5/1991 | Lotman ....................... 378/177 |
| 5,155,758 | A | * | 10/1992 | Vogl ............................. 378/209 |
| 5,270,530 | A | | 12/1993 | Godlewski et al. ......... 250/208.1 |
| 5,291,401 | A | | 3/1994 | Robinson ..................... 382/132 |
| 5,448,610 | A | | 9/1995 | Yamamoto et al. ............ 378/19 |
| 5,485,500 | A | | 1/1996 | Baba et al. ................. 378/98.2 |
| 5,596,437 | A | * | 1/1997 | Heins .......................... 359/144 |
| 5,638,521 | A | * | 6/1997 | Buchala et al. .............. 710/131 |
| 5,661,309 | A | * | 8/1997 | Jeromin et al. ............. 250/580 |
| 5,664,270 | A | * | 9/1997 | Bell et al. ....................... 5/600 |
| 5,687,717 | A | * | 11/1997 | Halpern et al. ............. 600/300 |
| 5,715,548 | A | | 2/1998 | Weismiller et al. ............. 5/624 |
| 5,806,111 | A | | 9/1998 | Heimbrock et al. .......... 5/86.1 |
| 5,844,961 | A | | 12/1998 | McEvoy et al. ............. 378/98.8 |
| 5,844,964 | A | | 12/1998 | Aichinger et al. ........... 378/207 |
| 5,864,708 | A | * | 1/1999 | Croft et al. ..................... 710/1 |
| 5,877,501 | A | * | 3/1999 | Ivan et al. ............. 250/370.09 |
| 5,933,888 | A | * | 8/1999 | Foster et al. .................... 5/604 |
| 5,996,149 | A | * | 12/1999 | Heimbrock et al. ........... 5/601 |
| 6,073,284 | A | * | 6/2000 | Borders ......................... 5/600 |
| 6,089,593 | A | * | 7/2000 | Hanson et al. .............. 280/650 |
| 6,151,732 | A | * | 11/2000 | Heimbrock et al. ........... 5/601 |
| 6,202,230 | B1 | * | 3/2001 | Borders ......................... 5/618 |
| 6,266,831 | B1 | * | 7/2001 | Heimbrock .................... 5/601 |
| 6,296,386 | B1 | * | 10/2001 | Heidsieck et al. .......... 378/189 |

FOREIGN PATENT DOCUMENTS

WO    WO 99/03396    1/1999

* cited by examiner

Primary Examiner—Robert H. Kim
Assistant Examiner—Allen C. Ho
(74) Attorney, Agent, or Firm—Bose McKinney & Evans LLP

(57) ABSTRACT

A patient support apparatus comprises a patient support portion, at least one digital x-ray cassette coupled to the patient support portion, the digital x-ray cassette having a first port, and a second port coupled to the first port of the digital x-ray cassette, the second port also coupled to one of the base and the patient support portion.

36 Claims, 10 Drawing Sheets

PATIENT SUPPORT WITH DIGITAL X-RAY CASSETTE

This application claims benefit of U.S. Provisional Application No. 60/124,611, filed Mar. 16, 1999, and U.S. Provisional Application No. 60/142,483, filed Jul. 6, 1999.

BACKGROUND AND SUMMARY OF THE INVENTION

The present invention relates to a patient support such as a hospital bed, surgical table, stretcher or chair. More particularly, the present invention relates to a patient support that is configured to receive a digital x-ray device.

Numerous types of hospital beds, surgical tables, hospital chairs, and other devices for supporting a patient are known. See, for example, U.S. Pat. No. 5,715,548 to Weismiller et al., U.S. patent application Ser. No. 09/188,785 entitled "Surgical Table", now U.S. Pat. No. 6,073,284, U.S. patent application Ser. No. 08/798,317 entitled "Ambulatory Care Chair", now U.S. Pat. No. 6,089,593, and U.S. patent application Ser. No. 09/009,522 entitled "Hospital Bed", now U.S. Pat. No. 5,933,888, U.S. patent application Ser. No. 08/895,847 entitled "Trauma Stretcher", now U.S. Pat. No. 5,996,149, and U.S. Pat. No. 5,806,111 to Heimbrock, the disclosures of which are incorporated herein by reference. Numerous types of digital x-ray systems are also known. See, for example, U.S. Pat. No. 5,844,964 to Aichinger et al.; U.S. Pat. No. 5,291,401 to Robinson; U.S. Pat. No. 5,485,500 to Baba et al.; U.S. Pat. No. 5,844,961 to McEvoy et al.; U.S. Pat. No. 5,448,610 to Yamamoto et al.; and U.S. Pat. No. 5,270,530 to Godlewski et al., the disclosures of which are incorporated herein by reference. Digital x-ray machines allow x-rays to be viewed and stored as digital images on computers without ever having to make a film copy. The digital x-ray images created by these x-ray machines can be e-mailed or otherwise transmitted between doctors or radiologists in different cities over an electrical communication network or via the Internet.

According to the present invention, a patient support apparatus includes a patient support portion and at least one digital x-ray cassette coupled to the patient support portion. In an illustrated embodiment, a transmitter is electrically coupled to the at least one digital x-ray cassette. The transmitter is coupled to the patient support portion. The transmitter can be either a port connector or an infrared transmitter.

In another illustrated embodiment, a storage device is electrically coupled to the at least one digital x-ray cassette. The storage device is coupled to the patient support portion and is used to store a digital image.

In another illustrated embodiment, the patient support portion is a mattress. In one version of this embodiment, the at least one digital x-ray cassette is located within an interior region of the mattress. In another version of this embodiment, the at least one digital x-ray cassette is coupled to a bottom surface of the mattress.

In another illustrated embodiment, the patient support portion includes a base and a deck coupled to the base. The at least one digital x-ray cassette is coupled to the deck. The port connector is coupled to one of the base and the deck. In one illustrated embodiment, the deck includes a back section, a seat section, and a leg section. The at least one digital x-ray cassette is coupled to one of the back section, the seat section, and the leg section. In one embodiment, separate digital x-ray cassettes are mounted to each of the back section, the seat section, and the leg section.

In another illustrated embodiment, the deck is formed to include a cassette receiving aperture configured to receive the at least one digital x-ray cassette, and a fastener is configured to hold the at least one digital x-ray cassette within the aperture. In yet another illustrated embodiment, the at least one digital x-ray cassette is mounted to a top surface of the deck. In still another illustrated embodiment, the at least one digital x-ray cassette is mounted to a bottom surface of the deck.

In a further illustrated embodiment, a plurality of digital x-ray cassettes are coupled to the patient support portion. In one version of this embodiment, the port connector is coupled to the plurality of digital x-ray cassettes through a switch. In another version of this embodiment, a plurality of port connectors are coupled to one of the base in the patient support portion. Each port connector is coupled to one of the digital x-ray cassettes.

Additional features and advantages of the invention will become apparent to those skilled in the art upon consideration of the following detailed description of the illustrated embodiments exemplifying the best mode of carrying out the invention as presently perceived.

DETAILED DESCRIPTION OF THE DRAWINGS

Figure 1:
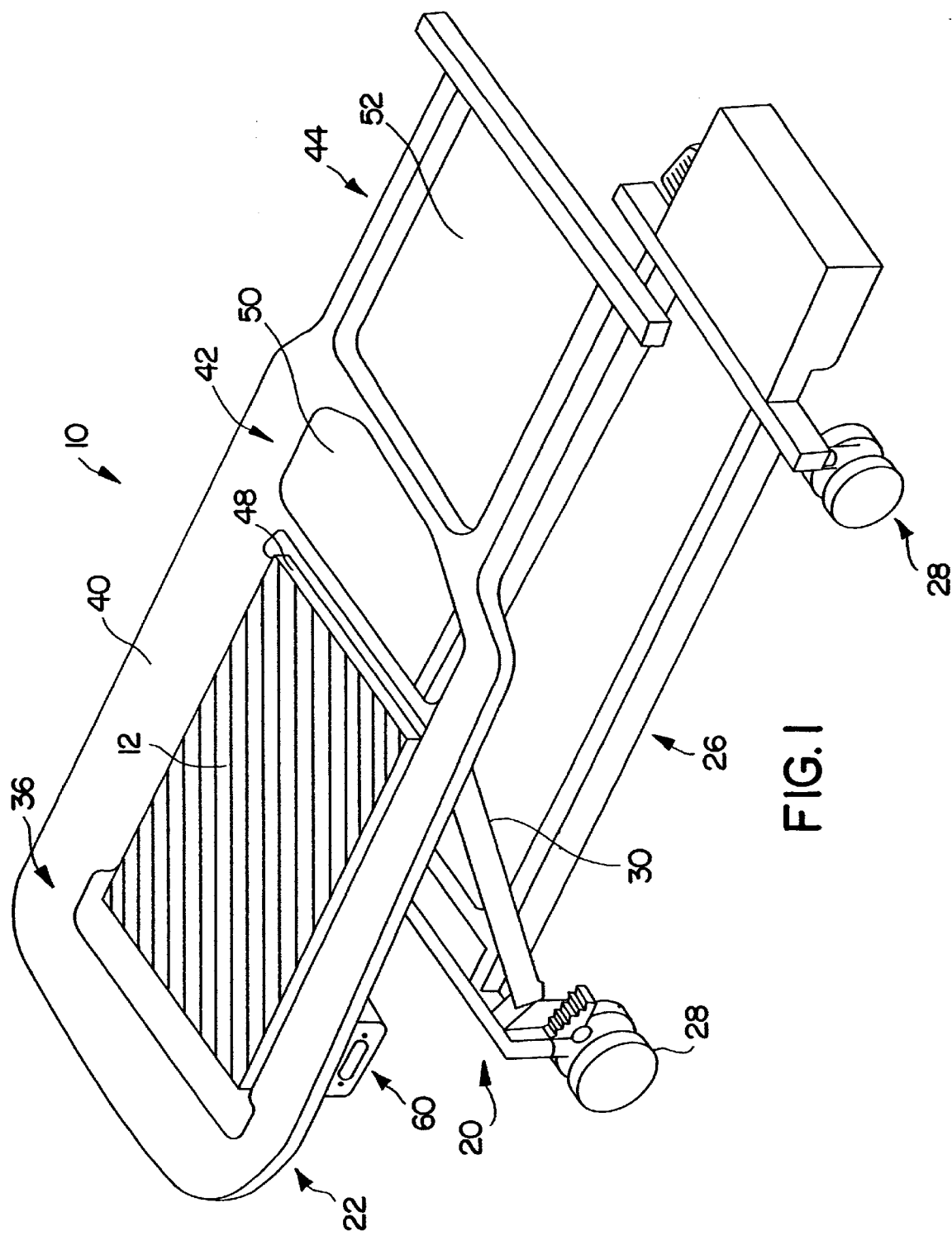
FIG. 1 is a perspective view of a hospital bed in accordance with the present invention showing the hospital bed having a patient-support portion that is formed to include three spaces for receiving three separate digital x-ray devices therein, a first digital x-ray device being positioned within the first space.

Referring now to the drawings, FIG. 1 illustrates one example of a hospital bed 10 that is configured to receive a digital x-ray receiver (also referred to as a digital x-ray cassette or image sensor) 12. As used in this description, identical elements have like reference numbers. Hospital bed (or patient support) 10 includes a base portion 20 and a patient-support portion 22 positioned above base portion 20. Base portion 20 includes a frame 26 mounted on casters 28 that allow hospital bed 10 to be rolled along the floor. Base portion 20 also includes at least one support arm 30 extending upwardly from frame 26 for supporting patient-support portion 22 at a variety of different heights relative to frame 26.

Patient-support portion 22 includes a deck 36 having a back section 40, a seat section 42, and a leg section 44. As shown in FIG. 1, back section 40 is formed to include a space 48 for receiving digital x-ray cassette 12. Seat section 42 and leg section 44 are also each formed to include a space 50, 52, respectively, for receiving an digital x-ray cassette, although no x-ray cassette is positioned in either space 50, 52. Thus, it is within the scope of this invention for multiple digital x-ray cassettes to be mounted to the bed. In addition, the digital x-ray cassette may be mounted at any location on the bed, including inside a mattress (see FIG. 9) or on the base portion 20. For example, a digital x-ray receiver may be mounted in one or more of the spaces 48, 50, 52 formed in the back, seat, and leg sections 40, 42, 44, on the patient-support portion 22, on frame 26, or on support arm 30.

Any suitable bracket, clamp, or fastener may be used to secure the digital x-ray cassette 12 to the deck 36. The digital x-ray cassette 12 is mounted in one of the receiving spaces 40, 50, or 52. In other embodiments, a deck of the patient support surface is an articulating deck including a plurality of deck sections which may be moved to various angular configurations. If a solid deck with no apertures is used, the digital x-ray cassette 12 is mounted to a top surface of the deck or to a bottom surface of the deck using suitable fasteners.

Figure 9:
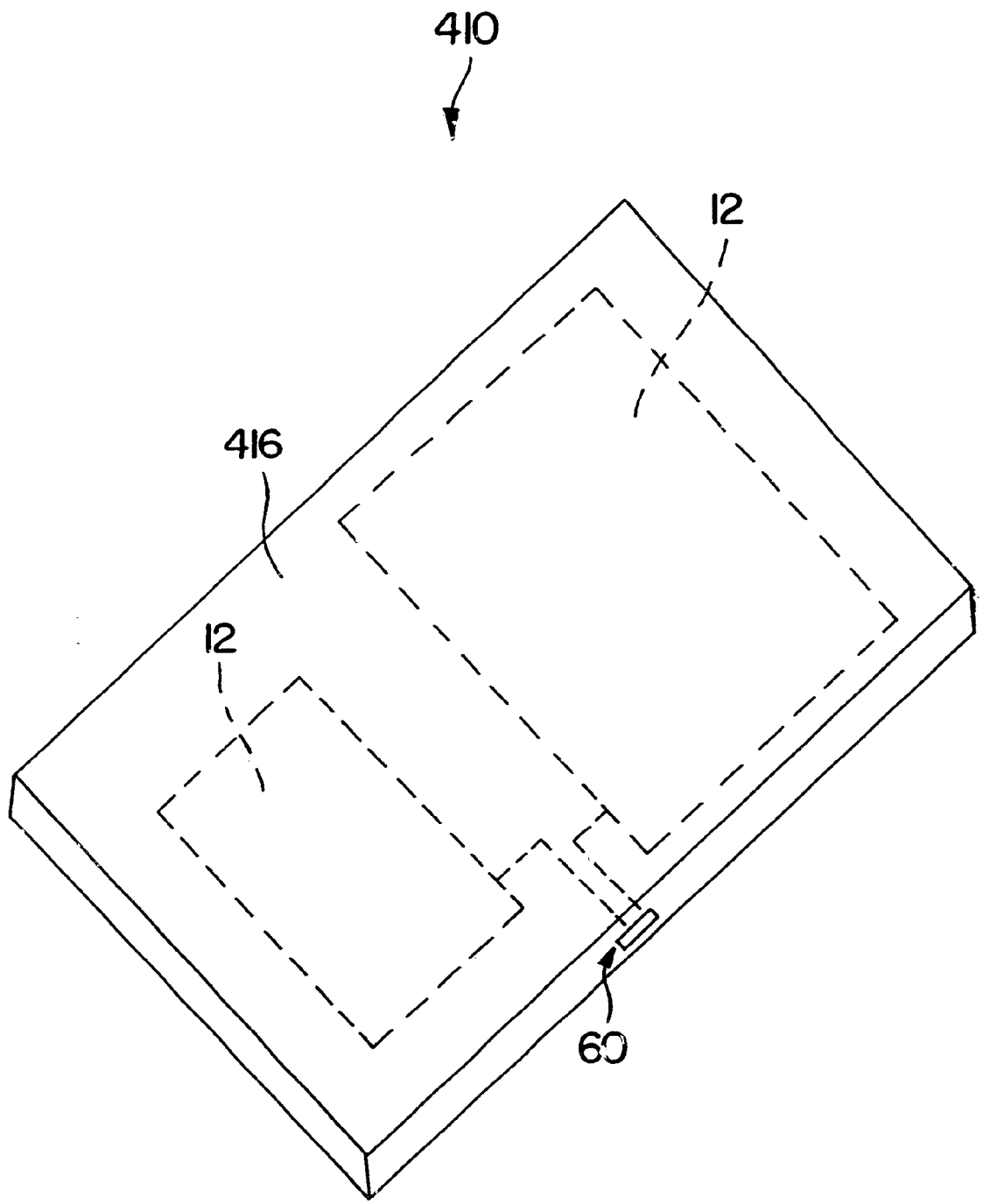
FIG. 9 is a top perspective view of a generic mattress that is formed to receive digital x-ray cassettes and a port connector therein.
Figure 10:
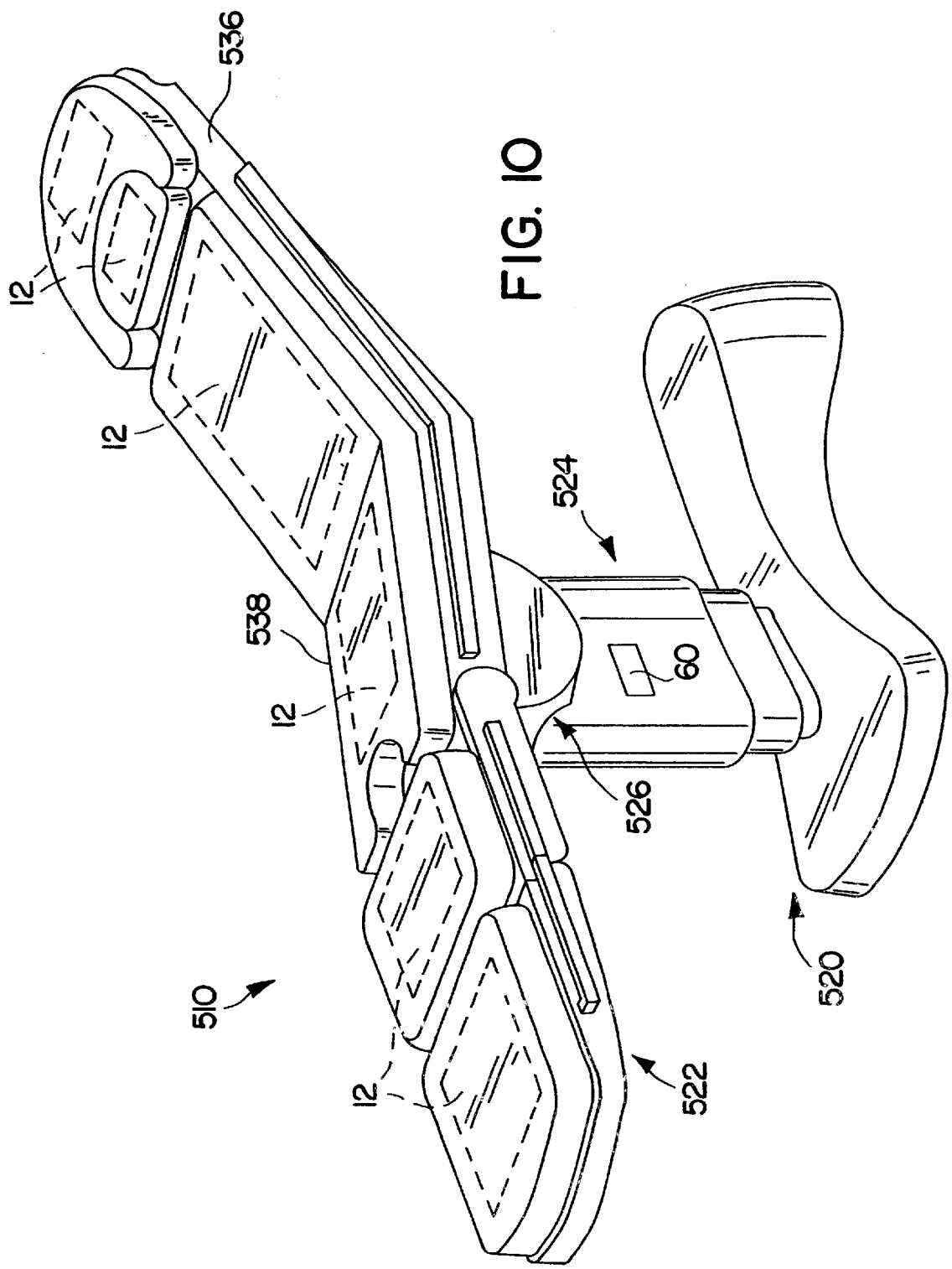
FIG. 10 is a perspective view of a surgical table apparatus configured to receive a plurality of digital x-ray cassettes and having a port connector mounted thereon.
Figure 11:
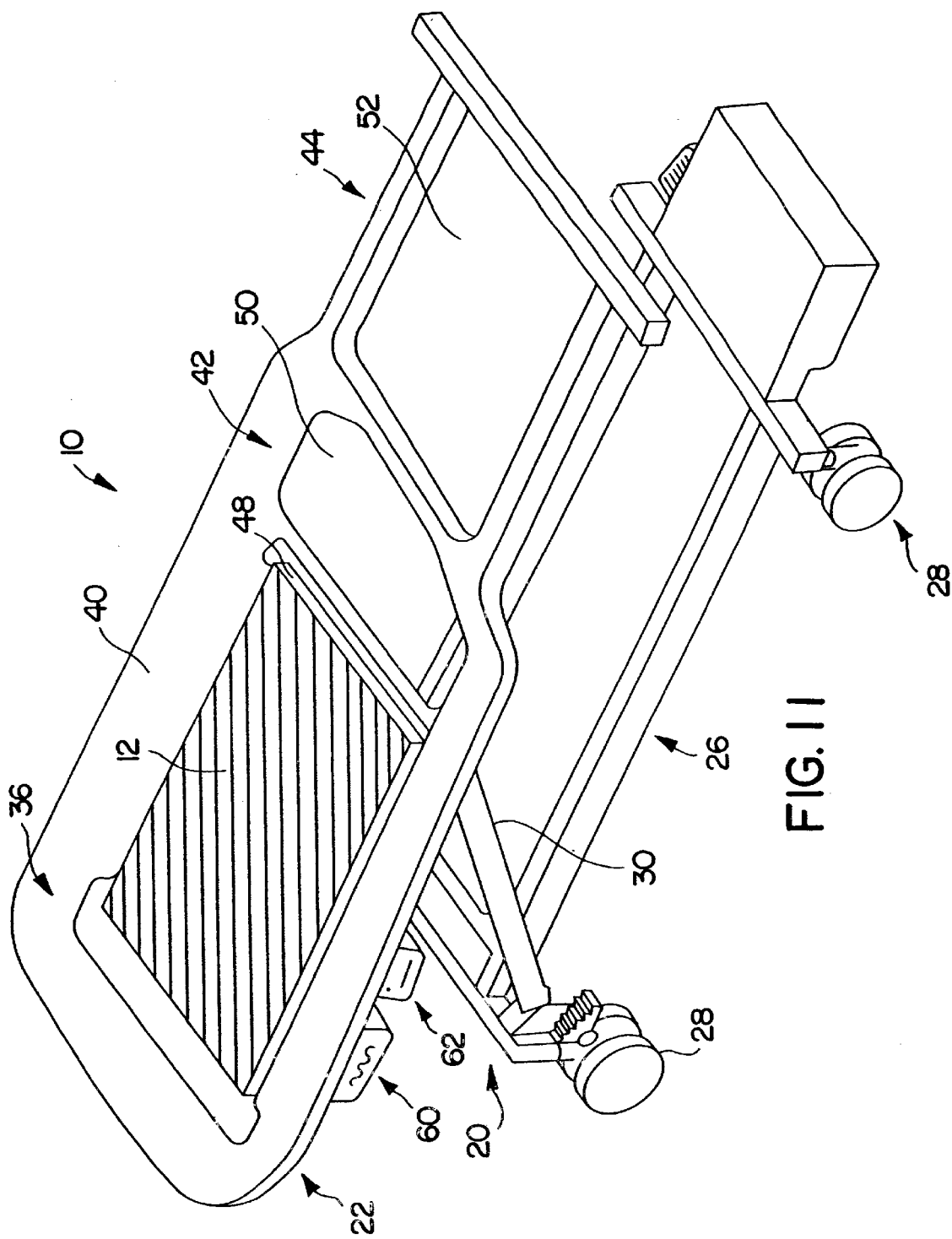
FIG. 11 is a perspective view of a hospital bed similar to FIG. 1 showing the hospital bed having both an infrared transmitter and a storage device.

A transmitter 60 and/or a storage device 62 may also be mounted at any location to patient support 10, as shown in FIGS. 1, 2, and 5–12. Transmitter 60 can be any type of device or apparatus for transmitting an electrical signal, such as a digital image, from one location to another. For example, transmitter 60 can be a port connector (FIG. 1) or an infrared transmitter (FIG. 11).

When transmitter 60 is configured as a port connector, port connector 60 is preferably a female RS-232 connector, although any other suitable connector may also be used. As shown in FIG. 1, port connector 60 is mounted to an underside of patient support portion 22. Port connector 60 is electrically coupled to the digital x-ray cassette 12. A x-ray generator (not shown) is connected to port connector 60 to take a digital x-ray. The digital image in the x-ray cassette 12 is then transmitted to the x-ray generator through port connector 60 so that the digital image is stored in the x-ray generator. As explained below, however, storage device 62 may be used so that the image can be stored at the patient support 10, instead of the x-ray generator. The image is then displayed on a monitor, or transmitted to an imaging department at a remote location via an existing communication system. Additional details relating to digital x-rays can be found in the patents listed above. As used herein, "digital x-ray device" refers to any piece of equipment used in connection with digital x-rays. For example, x-ray cassette 12, port connector 60, storage device 62 and x-ray generator (not shown) are all digital x-ray devices.

When transmitter 60 is configured as an infrared transmitter, as shown in FIG. 11, the digital image contained in digital x-ray cassette 12 can be communicated to a receiver (not shown) in a cordless manner. For example, an infrared receiver can be located in a hospital room and the infrared transmitter 60 can transmit the digital x-ray image from digital x-ray cassette 12 to the receiver without the need for a hard-wired connection. The digital x-ray image can then be communicated from the receiver to other areas within the hospital, such as a diagnostics lab, using standard communication systems or networks.

Figure 12:
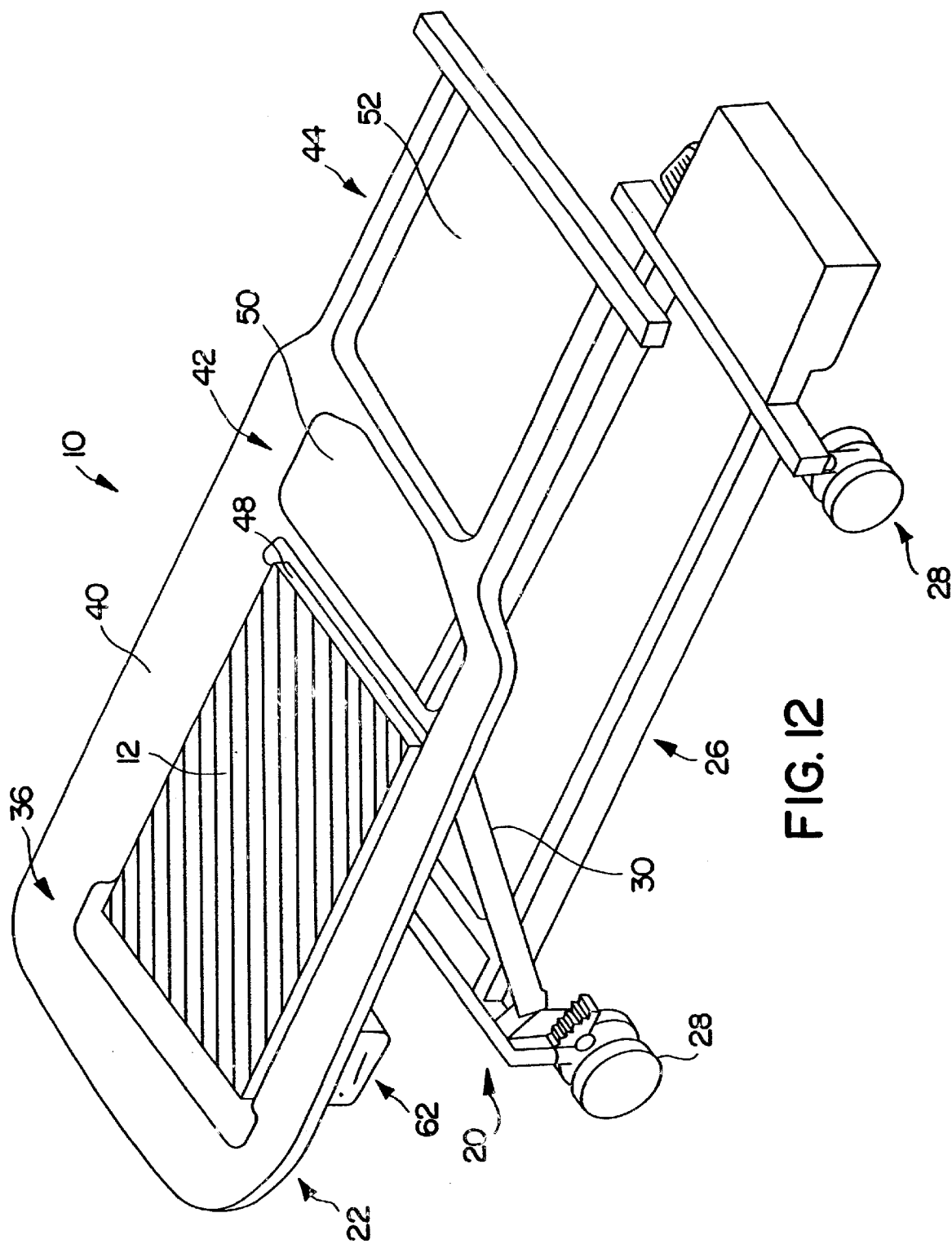
FIG. 12 is a perspective view of a hospital bed similar to FIG. 1 showing the hospital bed having a storage device.

Storage device 62, shown in FIGS. 11 and 12, allows a digital x-ray image to be stored at patient support 10. Storage device 62 preferably allows a floppy disk, CD-ROM, or DVD to be used to store the digital image, although any other suitable storage device may be used. As shown in FIG. 11, storage device 62 is mounted to patient support 10. Storage device 62 is electrically coupled to digital x-ray cassette 12. When a digital x-ray is taken by digital x-ray cassette 12, the digital x-ray image is stored by storage device 62. Thus, by using storage device 62, an x-ray generator would not be needed to store the x-ray image.

Furthermore, with sufficient memory in the storage unit, moving images could be stored. These moving images could be created by either moving the patient while shooting the x-ray or by moving the x-ray generator. An advantage of a moving image is that hairline fractures which are not seen at one angle may become visible at the proper angle.

Figure 2:
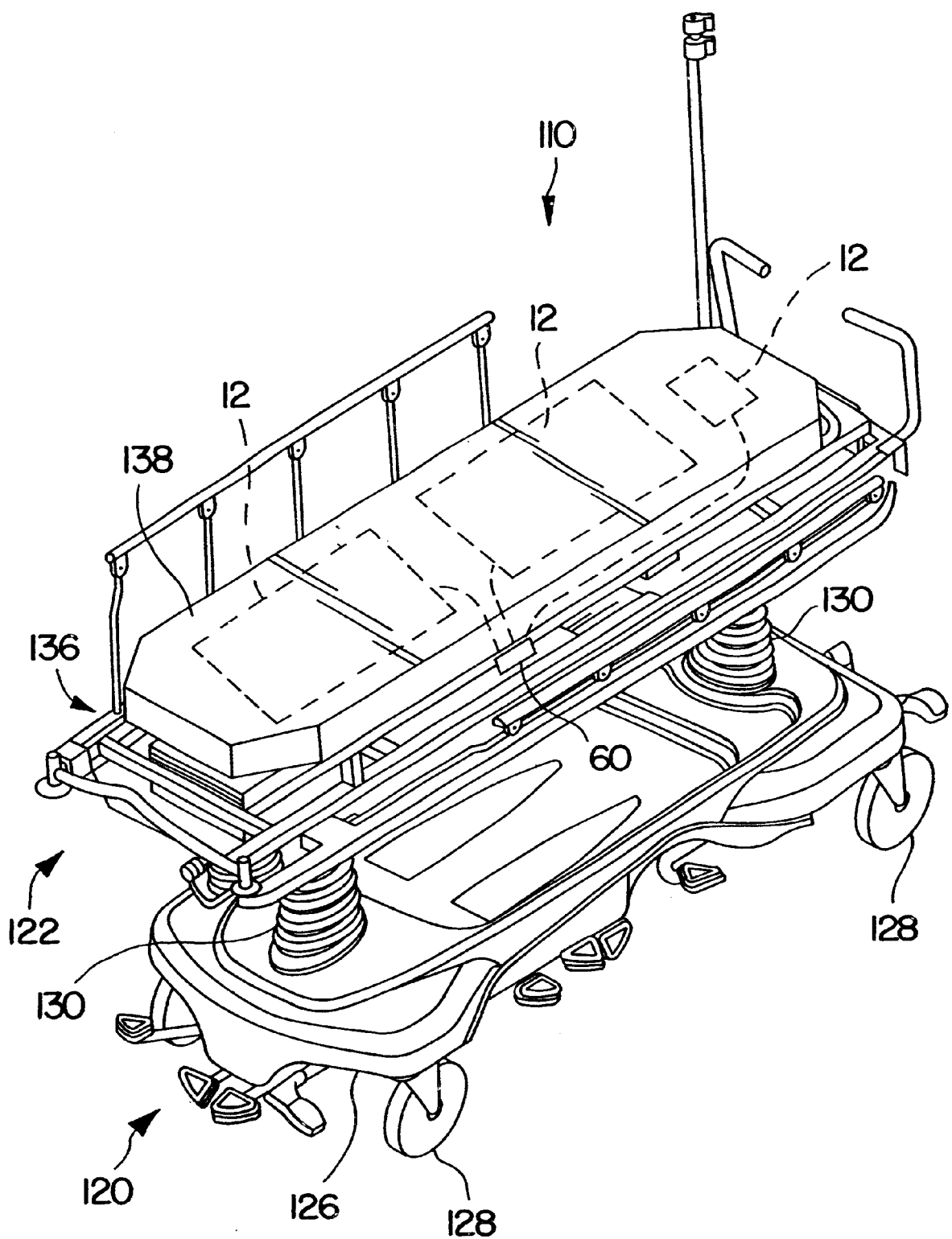
FIG. 2 is a perspective view of a stretcher in accordance with the present invention showing the stretcher having a patient-support portion including a deck and a mattress supported by the deck, the deck being formed to include a plurality of spaces for receiving digital x-ray devices therein.
Figure 3:
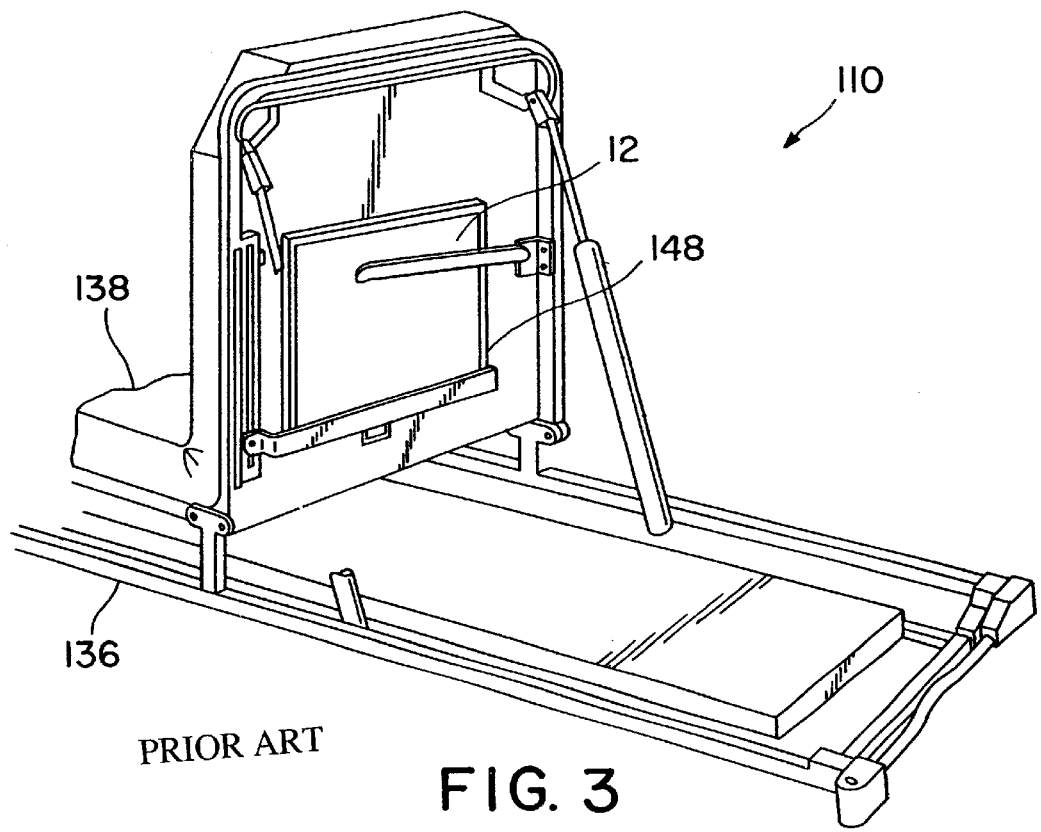
FIG. 3 is a perspective view of the stretcher of FIG. 2 being positioned in a sitting position to show one possible method of coupling a digital x-ray device to the stretcher.
Figure 4:
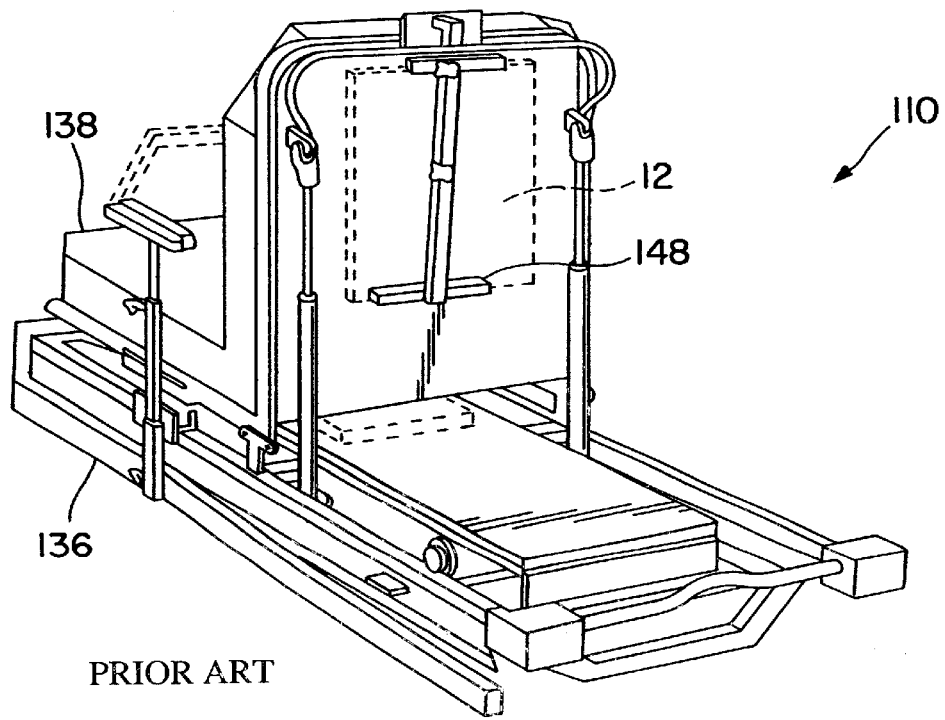
FIG. 4 is a view similar to FIG. 3 showing an alternative method of coupling a digital x-ray device to the stretcher.

A stretcher 110 configured to receive three digital x-ray cassettes 12 is shown in FIG. 2. Stretcher 110 is also considered to be a patient support because it is configured to support a patient. Stretcher 110 shown in FIGS. 2–4 is identical to the stretcher described in U.S. patent application Ser. No. 08/895,847 entitled "Trauma Stretcher Apparatus", now U.S. Pat. No. 5,996,149, except that stretcher 110 of the present invention has been modified to allow digital x-ray cassettes 12 to be coupled to it. As shown in FIG. 2, stretcher 110 includes a base portion 120 and a patient-support portion 122 positioned above base portion 120. Base portion 120 includes a frame 126 mounted on wheels 128 that allow stretcher 110 to be rolled along the floor. Base portion 120 also includes a pair of vertical support members 130 extending upwardly from frame 126 for supporting patient-support portion 122 at a variety of different heights relative to frame 126.

Patient-support portion 122 of stretcher 110 includes a deck 136 and a mattress 138 supported by deck 136, as shown in FIG. 2. As shown in FIGS. 3 and 4, deck 136 of stretcher 110 is formed to include a space 148 for receiving a digital x-ray cassette 12. As shown in FIG. 3, digital x-ray cassette 12 may be mounted to deck 136 in a manner that prevents digital x-ray cassette 12 from moving relative to deck 136. However, as shown in FIG. 4, digital x-ray cassette 12 may also be mounted to deck 136 such that digital x-ray cassette 12 is allowed to move relative to deck 136 upon adjustment by a user of the mounting members that couple the digital x-ray cassette 12 to the deck 136. It is understood that other suitable fasteners for securing the digital x-ray cassette 12 to the deck 136 may be used in accordance with the present invention.

Transmitter 60 is mounted to stretcher 110 at any location, much like hospital bed 10, as shown in FIG. 2. Once again, any suitable transmitter may be used. Transmitter 60 is electrically coupled to each digital x-ray cassette 12 so that a digital x-ray may be transmitted using any of the digital x-ray cassettes 12. Thus, transmitter 60 is coupled to a switch (not shown) to allow selection of the desired x-ray cassette 12 to be accomplished. A separate transmitter 60 may be coupled to each x-ray cassette 12, if desired. The digital image of the digital x-ray cassette 12 may be transmitted to an x-ray generator through port connector 60, as previously described, or to a remote receiver through infrared transmitter 60, as previously described.

Figure 5:
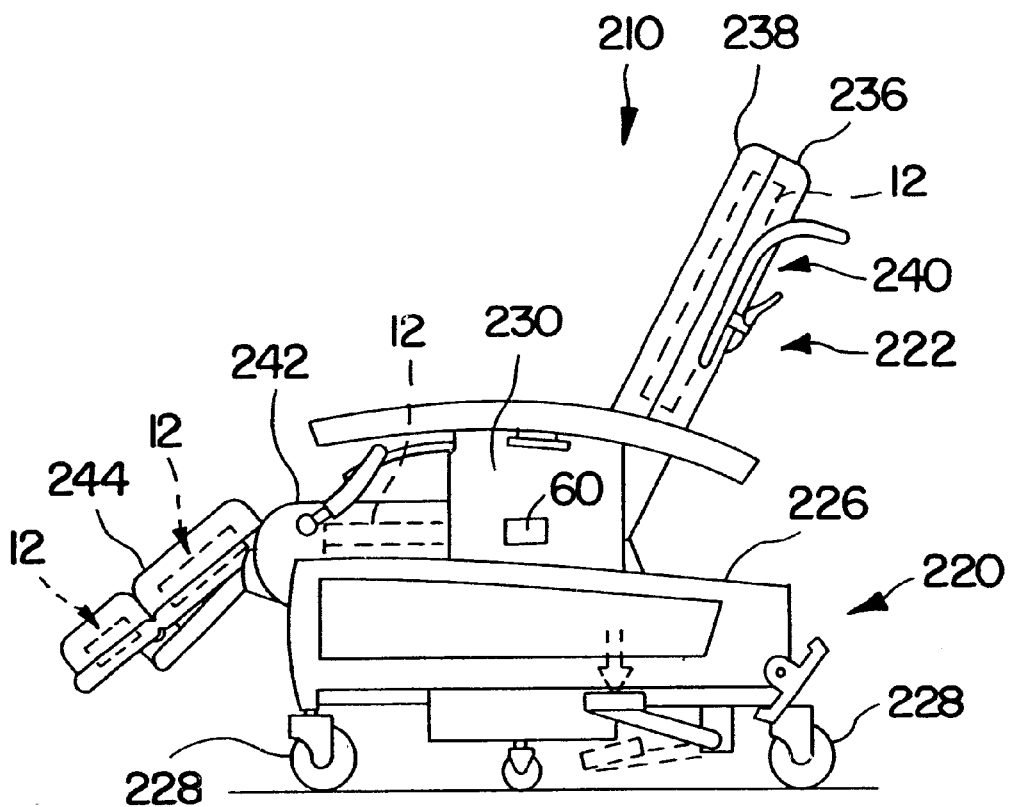
FIG. 5 is a side elevation view of an ambulatory care chair having back, leg, and seat sections that are formed to include spaces for receiving digital x-ray devices therein.
Figure 6:
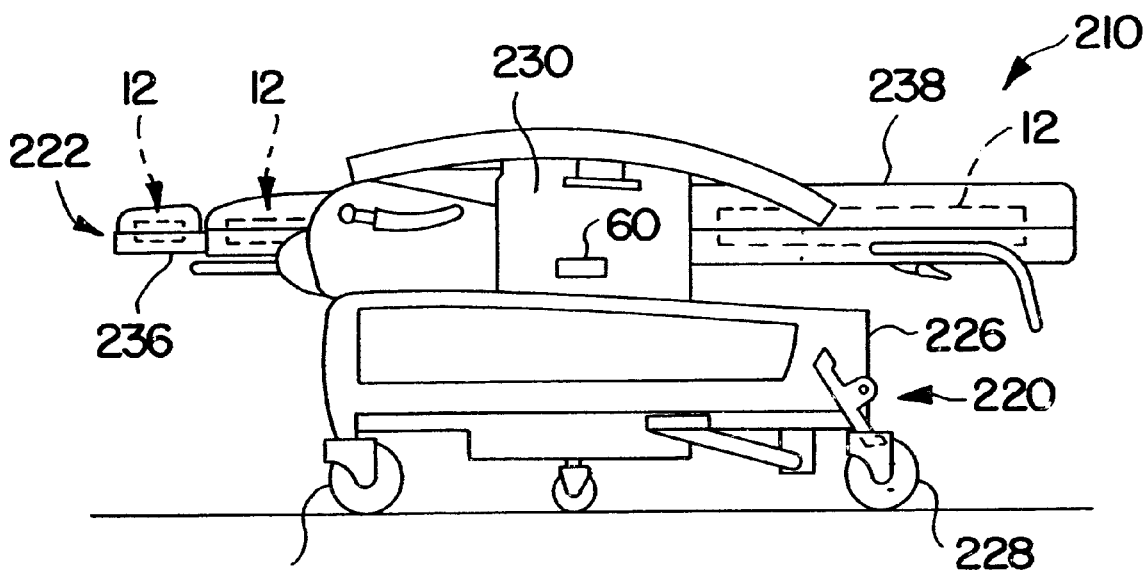
FIG. 6 is a view similar to FIG. 5 showing the ambulatory care chair in a horizontal sleeping position.
Figure 7:
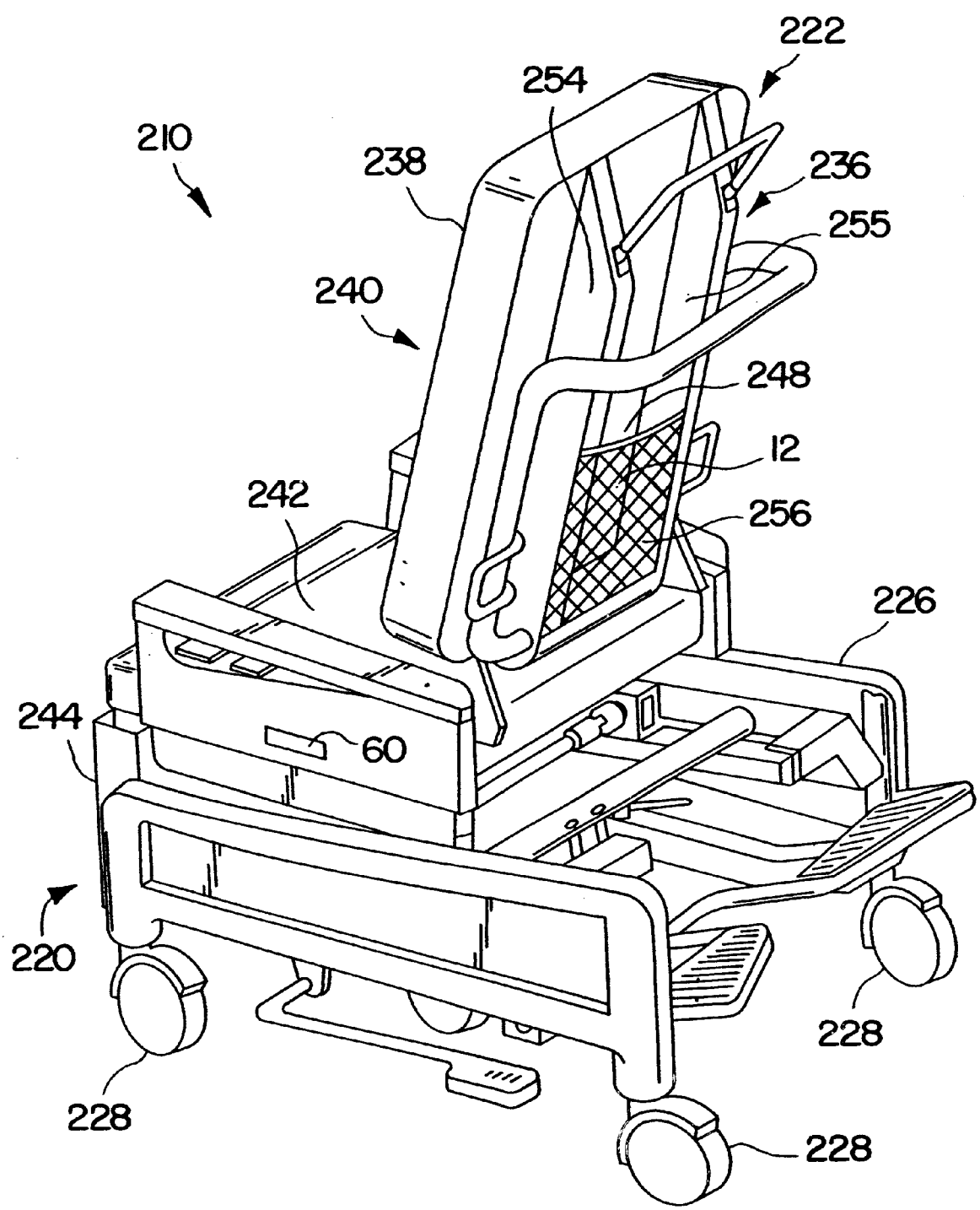
FIG. 7 is a perspective view of an ambulatory care chair similar to that of FIGS. 5 and 6 showing one possible method of coupling a digital x-ray cassette to the back portion of the chair.

An ambulatory care chair 210 having a plurality of digital x-ray cassettes 12 coupled thereto is illustrated in FIGS. 5–7. Ambulatory care chair 210 is identical to the ambulatory care chair described in U.S. patent application Ser. No. 08/798,317 entitled "Ambulatory Care Chair", now U.S. Pat. No. 6,089,593, except that the present ambulatory care chair 210 is configured to receive digital x-ray cassettes 12 as shown in FIGS. 5–7. As shown in FIGS. 5 and 6, ambulatory care chair 210 includes a base portion 220 and a patient-support portion 222 supported by base portion 220. Base portion 220 includes a frame 226 mounted on casters 228 that allow ambulatory care chair 210 to be rolled along the floor. Base portion 220 also includes two arm rests 230 extending upwardly from frame 226 to allow a patient (not shown) sitting on ambulatory care chair 210 to have their arms supported by arm rests 230.

Patient-support portion 222 of ambulatory care chair 210 includes a back section 240, a seat section 242, and a leg section 244, as shown in FIGS. 5 and 6. The back section 240 and the leg section 244 are each pivotable relative to the seat section 242 to allow ambulatory care chair 210 to move from a sitting position (FIG. 5) to a horizontal, lying position (FIG. 6). In preferred embodiments, back and seat sections 240, 242 are each configured to receive a single digital x-ray cassette 12 and leg section 244 is configured to receive two digital x-ray cassettes 12. However, any number of digital x-ray cassettes may be mounted to any portion of ambulatory care chair 210. In addition, although each of the digital x-ray cassettes 12 are shown to be mounted to patient-support portion 222, digital x-ray cassettes 12 may also be mounted to any part of base portion 220 including the arm rests 230.

Patient-support portion 222 of ambulatory care chair 210 includes a deck 236 and a mattress or cushion 238 supported by deck 236. Digital x-ray cassettes 12 are mounted to either deck 236 or mattress 238 or, as shown in FIGS. 5 and 6, digital x-ray cassettes may be positioned between deck 236 and mattress 238. One method of coupling digital x-ray cassettes 12 to patient-support portion 222 of ambulatory care chair 210 is shown in FIG. 7. As shown in FIG. 7, deck 236 is formed to include a space (or pocket) 248 for receiving digital x-ray cassette 12. Digital x-ray cassette 12 is then held in place on deck 236 by a pair of side walls 254, 255 and a net 256 extending between the side walls 254, 255, that define pocket 248, as shown in FIG. 7. Of course, a wide variety of methods may be used to mount digital x-ray cassette 12 to ambulatory care chair 210. Suitable fasteners may be used to secure the digital x-ray cassette 12 directly to the deck 236.

Chair 210 includes a transmitter 60 coupled to the chair 210 so that digital images may be transmitted from the x-ray cassette 12 to the appropriate x-ray device as discussed above. The images may be displayed on a monitor or transmitted to an imaging department at a remote location via the existing communications system.

Figure 8:
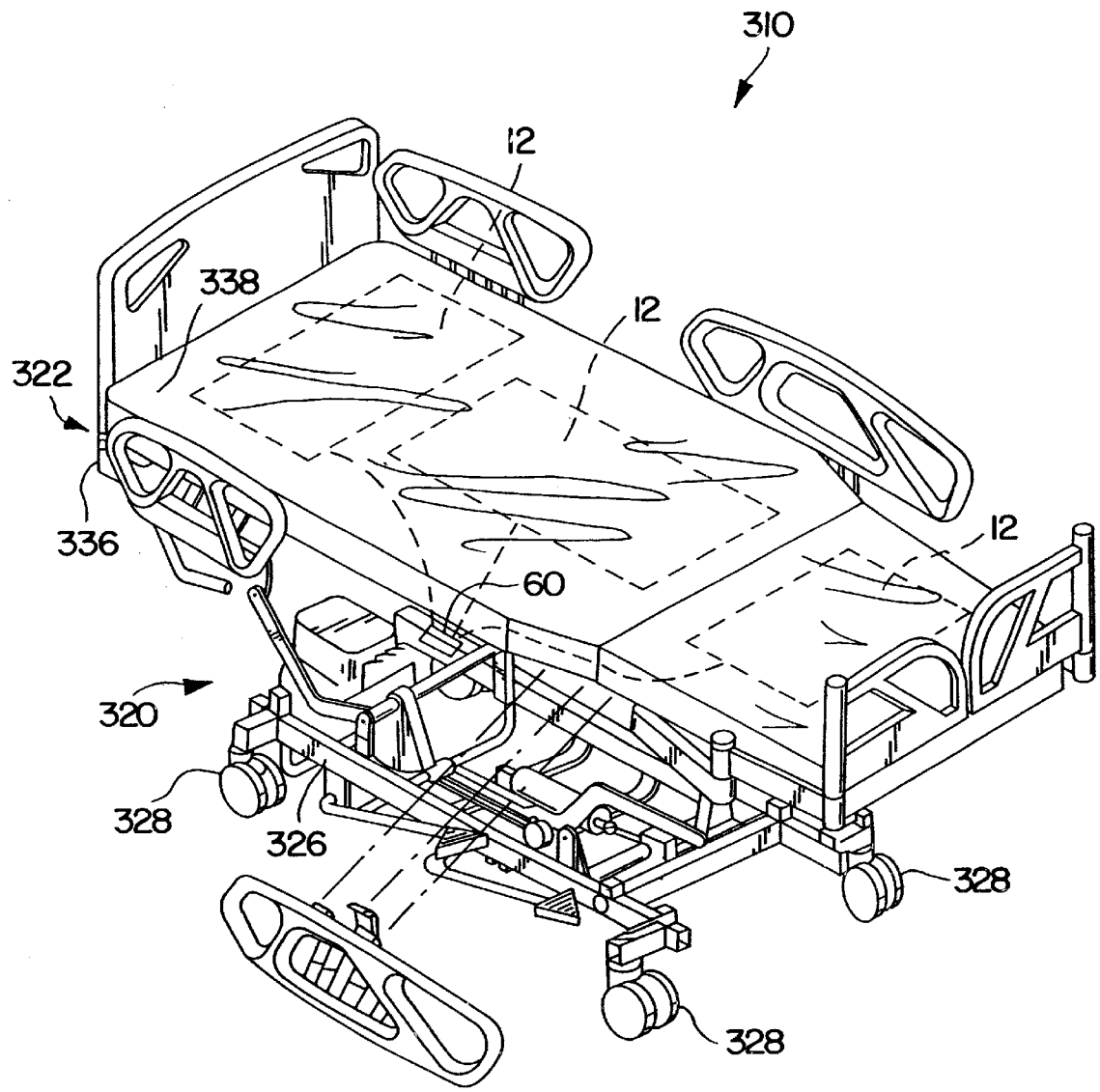
FIG. 8 is a perspective view of a chair bed having a variety of features, one of the features being a patient-support portion that is formed to include a plurality of spaces for receiving a plurality of digital x-ray devices therein.

A hospital chair bed 310 is illustrated in FIG. 8. The chair bed 310 shown in FIG. 8 is identical to the chair bed described in U.S. Pat. No. 5,715,548 to Weismiller, et al., except that chair bed 310 of the present invention has been modified to allow a plurality of digital x-ray cassettes 12 to be coupled to it. As shown in FIG. 8, chair bed 310 includes a base portion 320 and a patient-support portion 322 supported by base portion 320. Base portion 320 includes a frame 326 mounted on casters 328 that allow chair bed 310 to be rolled along the floor. Frame 326 is configured to allow patient-support portion 322 to be moved to a variety of positions as described in U.S. Pat. No. 5,715,548. For example, frame 326 allows patient-support portion 322 to be articulated to assume a variety of sitting and lying positions and also allows patient-support portion 322 to be positioned at a variety of different heights relative to the floor.

Patient-support portion 322 of chair bed 310 includes a deck 336 and a mattress 338 supported by deck 336. As discussed above for ambulatory care 210 and stretcher 110, each digital x-ray cassette 12 may be coupled to either mattress 338, deck 336, or any other part of chair bed 310. In preferred embodiments, the digital x-ray cassettes 12 are mounted to patient-support portion. 322 as shown in FIG. 8 either to deck 336 or within mattress 338. As shown in FIG. 8, a port connector 60 is also be mounted at any location on chair bed 310. Port connector 60 is identical to the previous port connectors described herein.

A generic mattress 410 enclosing two digital x-ray cassettes 12 and a transmitter 60 is shown in FIG. 9. As shown in FIG. 9, mattress 410 includes an outer cover 416 that illustratively conceals the digital x-ray cassettes 12. An opening is formed in cover 416, however, to allow transmitter 60 to be accessible to a user. Mattress 410 can be any type of mattress including an air mattress having inflatable bladders that allow the surface of mattress 410 to be moved and adjusted, a foam mattress, an air fluidized mattress, or a fluid-filled mattress. In the illustrated embodiment, the digital x-ray cassettes 12 are located within an interior region of the mattress 410. It is understood that the digital x-ray cassettes 12 may be mounted to a bottom surface of the mattress, outside of the cover 416, if desired.

FIG. 10 illustrates a surgical table 510 having a base 520 and a patient support portion 522 supported by the base 520. The base portion 520 includes a pedestal 524 and an angle adjustment mechanism 526 as shown in U.S. patent application Ser. No. 09/187,990, now U.S. Pat. No. 6,202,230, which is incorporated herein by reference. An articulating deck 536 and mattress 538 illustratively provide the patient support portion 522. Digital x-ray cassettes 12 are illustratively mounted to any desired section of the deck 536 or mattress 538. As discussed above, the digital x-ray cassettes 12 may be mounted directly to the deck 536 on a top or bottom surface of the deck 536, mounted in cassette receiving apertures formed in the deck 536, mounted within the mattress sections 538, or mounted to a bottom surface of the mattress sections 538. Each of the x-ray cassettes 12 is coupled to a port connector 60 which provides an output to the digital x-ray device as discussed above. The images are then displayed on a monitor or transmitted to an imaging department at a remote location via an existing communications system as discussed above.

Although the present invention has been described with reference to FIGS. 1–12 which show an illustrative hospital bed 10, an illustrative stretcher 110, an illustrative ambulatory care chair 210, an illustrative chair bed 310, an illustrative mattress 410, and an illustrative surgical table 520, each having a patient-support portion configured to receive at least one digital x-ray cassette 12, the scope of the present invention covers any type of patient-support apparatus having at least one digital x-ray device coupled thereto. For example, virtually any type of hospital bed, surgical table, hospital chair, wheel chair, stretcher, or other patient support could be modified to receive the digital x-ray cassette 12. In addition, any of the patient support apparatuses may include either a transmitter 60 or a storage device 62 or both.

The present invention facilitates taking x-ray images of a patient on the patient support apparatus. Since the digital x-ray cassettes 12 are coupled to the patient support as discussed above, the doctor or radiologist simply activates the x-ray generator so that a digital x-ray image is captured by the digital x-ray cassettes 12. The digital image can then be transmitted to a digital storage device which is located either on the patient support or remotely from the patient support. If a port connector 60 is used, the cable is disconnected from the port connector 60 after the digital x-ray data is stored. Therefore, the patient is not disturbed while the x-ray is being taken. The digital storage device 62 may be included in the x-ray generator or a separate device. For example, as shown in FIGS. 11 and 12, a digital storage device 62 can be mounted to the patient support 10 regardless of the kind of transmitter 60 being used. The stored image can then be displayed on a monitor or transmitted to a remote location through an existing communication network.

The patient support apparatus could also be configured to include a cassette holder similar to the one shown in FIG. 3 of U.S. Pat. No. 5,844,961. Such a configuration would allow the digital x-ray cassette 12 to be easily installed and removed from any of the patient support apparatuses. In addition, if a digital x-ray cassette similar to the one shown in the '961 patent is used, a separate transmitter might not be needed because, as shown in FIG. 3 of the '961 patent, the digital cassette 200 includes communications port 305.

Although the invention has been described in detail with reference to certain illustrated embodiments, variations and modifications exist within the scope and spirit of the invention as described and defined in the following claims.

What is claimed is:

1. A patient support apparatus comprising:
   a base;
   a patient support portion supported by the base;
   a digital x-ray cassette coupled to the patient support portion, the digital x-ray cassette having a first port; and
   a second port coupled to the first port of the digital x-ray cassette, the second port also coupled to one of the base and the patient support portion, wherein the second port provides digital x-ray cassette data to an external system.

2. The apparatus of claim 1, wherein the patient-support portion includes a back section, a seat section, and a leg section, the digital x-ray cassette being coupled to one of the back section, the seat section, and the leg section.

3. The apparatus of claim 2, wherein separate digital x-ray cassettes are mounted to each of the back section, the seat section, and the leg section.

4. The apparatus of claim 1, wherein the patient support portion includes a deck coupled to the base and a mattress located on the deck, the digital cassette being coupled to the deck.

5. The apparatus of claim 4, wherein the deck is formed to include a cassette receiving aperture configured to receive the digital x-ray cassette, and a fastener configured to hold the digital x-ray cassette within the aperture.

6. The apparatus of claim 4, wherein the at least one digital x-ray cassette is mounted to a top surface of the deck.

7. The apparatus of claim 4, wherein the digital x-ray cassette is mounted to a bottom surface of the deck.

8. The apparatus of claim 1 wherein the patient support portion includes a deck coupled to the base and a mattress located on the deck, the digital x-ray cassette being coupled to the mattress.

9. The apparatus of claim 8, wherein the second port is also coupled to the mattress.

10. The apparatus of claim 1, wherein the patient support apparatus is a hospital bed.

11. The apparatus of claim 1, wherein the patient support apparatus is a stretcher.

12. The apparatus of claim 1, wherein the patient support apparatus is a chair.

13. The apparatus of claim 1, wherein the patient support apparatus is a surgical table.

14. The apparatus of claim 1, wherein a plurality of digital x-ray cassettes are coupled to the patient support portion, each of the plurality of digital x-ray cassettes having an associated first port.

15. The apparatus of claim 14, wherein the second port is coupled to the each of the associated first ports through a switch.

16. The apparatus of claim 14, wherein a plurality of second ports are coupled to one of the base in the patient support portion, each second port being coupled to one of the associated first ports.

17. A patient support apparatus comprising:
   a mattress;
   at least one digital x-ray cassette coupled to the mattress; and
   a port connector electrically coupled the at least one digital x-ray cassette, the port connector also being coupled to the mattress.

18. The apparatus of claim 17, wherein the mattress comprises inflatable bladders.

19. The apparatus of claim 18, wherein the at least one digital x-ray cassette is located within an interior region of the mattress.

20. The apparatus of claim 18, wherein the at least one digital x-ray cassette is coupled to a bottom surface of the mattress.

21. The apparatus of claim 20, wherein the patient support apparatus further comprises:
   a base; and
   a deck coupled to the base, the mattress being coupled to the deck.

22. The apparatus of claim 17, wherein the mattress is an air fluidized mattress.

23. The apparatus of claim 17, wherein the mattress is a fluid filled mattress.

24. The apparatus of claim 17, wherein the at least one digital x-ray cassette is located within an interior region of the mattress.

25. The apparatus of claim 17, wherein the mattress comprises:
   a top surface on which a patient is supported; and
   a bottom surface, the at least one digital x-ray cassette coupled to the bottom surface of the mattress.

26. The apparatus of claim 17, wherein a plurality of digital x-ray cassettes are coupled to the mattress.

27. The apparatus of claim 26, wherein the port connector is coupled to the plurality of digital x-ray cassettes through a switch.

28. The apparatus of claim 26, wherein a plurality of port connectors are coupled the mattress, each port connector being coupled to one of the digital x-ray cassettes.

29. A patient support apparatus comprising
a base;
a patient support portion supported by the base and adapted to support a patient thereon, the patient support portion being formed to include a space;
a digital x-ray cassette coupled to the patient support portion and positioned to lie in the space, the digital x-ray cassette having a first port;
a second port coupled to the first port of the digital x-ray cassette, the second port also coupled to one of the base and the patient support portion; and
a data processing device electrically coupled to the second port.

30. The patient support apparatus of claim 29, wherein the data processing device comprises a storage device electrically coupled to the digital x-ray cassette and configured to store a digital x-ray image.

31. The patient support apparatus of claim 29, wherein the data processing device comprises a transmitter electrically coupled to the digital x-ray cassette and configured to transmit a digital x-ray image taken by the digital x-ray cassette to a remote location.

32. The patient support apparatus of claim 30, wherein the data processing device further comprises a transmitter electrically coupled to the digital x-ray cassette and configured to transmit a digital x-ray image taken by the digital x-ray cassette to a remote location.

33. The patient support apparatus of claim 32, wherein the transmitter is an infrared transmitter.

34. A patient support apparatus comprising:
a base;
a patient support portion supported by the base, the patient support portion including a deck coupled to the base, the deck having a top surface;
a mattress located on the top surface of the deck;
at least one digital x-ray cassette coupled to the patient support portion and mounted to the top surface of the deck of the patient support portion; and
a port connector electrically coupled to the at least one digital x-ray cassette, the port connector being coupled to one of the base and the patient support portion.

35. A patient support apparatus comprising:
a base;
a patient support portion supported by the base, including a deck coupled to the base;
a mattress located on the deck;
at least one digital x-ray cassette coupled to the patient support portion and the mattress; and
a port connector electrically coupled to the at least one digital x-ray cassette, the port connector being coupled to one of the base and the patient support portion.

36. The apparatus of claim 35, wherein the port connector is also coupled to the mattress.

* * * * *